United States Patent
Lan et al.

(10) Patent No.: US 8,362,081 B2
(45) Date of Patent: Jan. 29, 2013

(54) METHODS FOR TREATING HEMORRHAGIC CONDITIONS

(76) Inventors: Guihua Lan, Yunnan Province (CN); Ping Chen, Yunnan Province (CN); Qiu Sun, Yunnan Province (CN); Song Fang, Yunnan Province (CN)

( * ) Notice: Subject to any disclaimer, the term of this patent is extended or adjusted under 35 U.S.C. 154(b) by 343 days.

(21) Appl. No.: 12/651,241

(22) Filed: Dec. 31, 2009

(65) Prior Publication Data
US 2011/0160307 A1 Jun. 30, 2011

(51) Int. Cl.
*A61K 31/195* (2006.01)
*A61K 36/258* (2006.01)

(52) U.S. Cl. .......................... 514/563; 514/834; 424/728

(58) Field of Classification Search .................. 514/563, 514/834; 424/728
See application file for complete search history.

(56) References Cited

FOREIGN PATENT DOCUMENTS
CN 101380294 A * 3/2009

OTHER PUBLICATIONS
English Translation of CN 101380294 A (2009).*

* cited by examiner

*Primary Examiner* — Kevin E Weddington
(74) *Attorney, Agent, or Firm* — Daniel W. Celander; Celander Lawfirm Ltd.

(57) ABSTRACT

A method of treating a hemorrhagic condition in a subject in need thereof, comprising administering a composition comprising a therapeutically effective amount of Dencichine, a co-solvent, a dispersion supporter, and optionally a cryoprotectant. Compositions and formulations comprising a solid dispersion composition of Dencichine and methods for preparation of same are also described.

7 Claims, No Drawings

METHODS FOR TREATING HEMORRHAGIC CONDITIONS

BACKGROUND

Bleeding is a common medical problem that requires immediate attention. Bleeding caused by traumatic violence, routine surgical operation or complications of certain diseases leads to lower amounts of circulating blood, cell hypoxia, metabolic and nutrient imbalances in tissue, and damage to the function of vital organs.

Compositions and methods for arresting bleeding and hemorrhagic conditions are presently the focus of clinical study. Operative or non-operative treatments are required for bleeding control. The non-operative treatments consist of medicine-based treatments (for example, haemostatic medicine for injection and medicine for blood vessel contraction), mechanical treatments (for example, hemoclip and humoring methods), and physical treatments (for example, electro-coagulation and heat therapy).

Various haemostatic medications are used presently in the clinical setting, such as medicines for blood vessel contraction (for example, Pituitrin and Ephedrin), medicines for lowering the brittleness and permeability of blood vessel walls (for example, Rutin, Ethamsylate, and Adrenal Cortical Hormone), medicines for blood coagulation (for example, Thrombin and Fibrin Sponge), and medicines for enhancing platelet production (for example, Thrombopoietin).

Molecular approaches are being used to study many aspects of the mechanism of haemostasis. For example, several haemostatic medications have been manufactured from animal and plant compositions. Synthetic haemostats also have been developed based on the mechanism of blood coagulation. However, those haemostatic medications do not satisfy the clinical needs for decreasing the amount of bleeding in patients without having an attendant side effect of toxicity. Therefore, a haemostatic medication with high efficacy and low toxicity is needed.

SUMMARY

In a first aspect, the invention is a method of treating a hemorrhagic condition, comprising administering a composition comprising a therapeutically effective amount of Dencichine, a co-solvent, and a dispersion supporter.

In a second aspect, the invention is a composition for treating or preventing a bleeding disorder, wherein the composition comprises a therapeutically effective amount of Dencichine, a co-solvent, and a dispersion supporter.

In a third aspect, the invention is a method for preparing a solid dispersion composition of Dencichine, comprising dissolving Dencichine in a medium comprising a co-solvent to provide a first solution; dissolving a dispersion supporter into the first solution to provide a second solution; dissolving a cryprotectant into the second solution to provide for a third solution; and filtering and drying the third solution to provide the solid dispersion composition of Dencichine.

In a fourth aspect, the invention is a method for preparing a solid dispersion composition of Dencichine, comprising: dissolving Dencichine into a co-solvent to provide a first solution; mixing the first solution into a second solution comprising a dispersion supporter to provide a third solution; filtering the third solution to provide a filtrate; subjecting the filtrate to −40° C.; and freeze-drying the filtrate to provide the solid dispersion composition of Dencichine. In a preferred embodiment, the co-solvent comprises aqueous ammonium hydroxide and the dispersion supporter comprises mannitol.

DETAILED DESCRIPTION

The object of this invention is to provide compositions of Dencichine for treating hemorrhagic disease and bleeding conditions generally. Dencichine is one haemostatic agent present in well-known traditional Chinese medicinal herbs that has been developed to arrest bleeding. The compositions enable Dencichine to quickly disperse within the body, thus promoting its absorption and improving its effect on bleeding control. The compositions of the present invention also provide efficient delivery of Dencichine to the site of action without deleterious side effects of toxicity.

A key feature of the present invention is the development of a solid dispersion composition of Dencichine. The composition provides Dencichine in a form amenable for storage as well as inclusion in a variety of formulations for administration. The solid dispersion composition of Dencichine comprises from about 1 to about 5 parts (wt/wt) Dencichine, from about 0.4 to about 2 parts (wt/wt) co-solvent, from about 0.5 to about 2.5 parts (wt/wt) dispersion supporter, and from about 0.1 to about 0.5 parts (wt/wt) cryoprotectant.

The solid dispersion composition of Dencichine is fast-acting, displays excellent efficacy for stopping bleeding, and shows low toxicity. For example, a 1 mg dose of solid dispersion composition of Dencichine, which contains about 0.5 mg of Dencichine by weight (see Example 1), displays comparable pharmacologic activity for stopping bleeding as observed with a 25 mg dose of Sodium Dencichine (see Examples 2-5). Thus, the solid dispersion composition of Dencichine displays surprising and superior pharmacological activity than would be expected, as adjudged from the pharmacological activity of the composition of the invention, having a 50-fold lower amount of Dencichine when compared conventional compositions containing pure active ingredient.

Suitable co-solvents include simple salts and buffering salts. Examples of co-solvents comprising simple salts include NaCl, KCl, $CaCl_2$, $MgCl_2$, and the like, as well as mixtures thereof. Examples of co-solvents comprising buffering salts include $CH_3CO_2Na$, $CH_3CO_2K$, $CH_3CO_2NH_4$, $NaH_2PO_4$, $Na_2HPO_4$, $KH_2PO_4$, $K_2HPO_4$, $NaHCO_3$, $Na_2CO_3$, $KHCO_3$, $K_2CO_3$, $(NH_4)HCO_3$, $(NH_4)_2CO_3$, $NH_4OH$, and the like, as well as mixtures thereof. A preferred co-solvent comprises a buffering salt. More preferably, the co-solvent comprises $(NH_4)_2CO_3$ or $NH_4OH$.

Suitable co-solvent dissolution media for preparing the solid dispersion composition of Dencichine include water and physiologically compatible water-organic solvent mixtures, such as water-ethanol. A preferred co-solvent dissolution medium comprises water.

Suitable dispersion supporters include polyethylene glycol, mannitol, polylactic acid, glycerol monostearate, gelatin, poloxamers (for example, P 188 and P 407), stearic acid and conjugate base salts thereof (such as calcium stearate and magnesium stearate), sodium alginate, water-soluble chitosan, and the like, as well as mixtures thereof. Preferred dispersion supporters are polyethylene glycol 6000 (PEG 6000), mannitol, polylactic acid, gelatin, poloxamers (for example, P 188 and P 407), stearic acid, glycerol monostearate, sodium alginate, water-soluble chitosan, and mixtures thereof.

Suitable cryoprotectants include sugars, such as mannose, glucose, fructose, sucrose, fucose, and the like, as well as mixtures thereof. Preferred cryoprotectants are sucrose, fucose, and mixtures thereof.

The solid dispersion composition of Dencichine is prepared as described in the Examples. A method for preparing a preferred composition is described briefly. Dencichine (for example, 2.0 g) is added to co-solvent comprising 1% (wt/vol) aqueous ammonium bicarbonate solution (for example, $(NH_4)_2CO_3$ (0.8 g) dissolved in water (80 ml)). The mixture is stirred to effect dissolution, thereby yielding a first solution. A dispersant supporter, such as PEG 6000 (for example, 1.0 g), is added to the resultant first solution. The mixture is stirred to effect dissolution, thereby yielding a second solution. A cryoprotectant, such as sucrose (for example, 0.2 g), is added to the resultant second solution. The mixture is stirred to effect dissolution, thereby yielding a third solution. The resultant third solution is filtered to remove any insoluble particulate matter, thereby providing a filtrate. The filtrate is subjected to freeze-drying to provide the solid dispersion composition of Dencichine.

A more preferred solid dispersion composition of Dencichine comprises Dencichine (for example, about 1 part (wt/wt)), a co-solvent comprising $NH_4OH$ (for example, about 0.15 part (wt/wt)), and a dispersion supporter comprising mannitol (for example, about 1 part (wt/wt)). The inclusion of $NH_4OH$ as co-solvent and mannitol as dispersion supporter eliminates the requirement for a cryoprotectant in the solid dispersion composition of Dencichine.

A method for preparing this preferred composition is described briefly. A 1% (wt/vol) co-solvent solution is prepared by dissolving $NH_4OH$ (0.15 g) in water (15 ml). Dencichine (1.0 g) is added to this co-solvent solution, and the mixture is stirred to effect dissolution, thereby yielding a first solution. The dispersant supporter, mannitol (1.0 g), is dissolved in water (30 ml) to obtain a second solution. The first solution is slowly added to the second solution and the mixture is stirred 10 to 60 min. A sufficient quantity of water is then added to the resultant mixture with stirring until a final solution weight of 100 g is achieved, thereby yielding a third solution. The resultant third solution is filtered to remove any insoluble particulate matter, thereby providing a filtrate. The filtrate is subjected to −40° C. for twenty-four hours and then subjected to freeze-drying to provide the solid dispersion composition of Dencichine.

Dencichine (3-N-oxalyl-L-2,3-diaminopropanoic acid, or β-N-oxalyl-L-α,β-diaminopropionic acid in biological literature) used in these solid dispersion compositions is prepared according to methods and procedures known in the art. A preferred preparation of Dencichine is obtained using chemical synthesis methods described in China Patent Application Nos. 00109991 and 00109992, entitled "Synthesis method for preparing high-effective hemostatic notogiseng extract" and "Synthesis preparation method of high-effective hemostatic notoginseng extract," respectively, both of which were filed Aug. 10, 2000 by Guihua Lan, Song Fang, and Peng Chen, and both of which subsequently published Apr. 25, 2001 as China Patent Application Publication Nos. 1292376 and 1292377, respectively. The solid dispersion compositions of Dencichine described herein are prepared using Dencichine that is manufactured according to the synthetic methods described in China Patent Application Nos. 00109991 and 00109992, which are incorporated by reference herein in their entirety.

The present invention contemplates pharmaceutical or nutraceutical formulations of the solid dispersion composition of Dencichine for administration to mammals for treating hemorrhagic conditions, bleeding disorders and related symptoms. In a preferred embodiment, a composition for administration is a pharmaceutical or nutraceutical composition, preferably in a single unit dosage form. Pharmaceutical or nutraceutical compositions and single unit dosage forms can comprise an effective amount of one or more prophylactic or therapeutic agents, and a typically one or more pharmaceutically acceptable carriers or excipients or diluents.

The term "pharmaceutically acceptable" means approved by a regulatory agency of the Federal or a state government (for example, the U.S. Food and Drug Administration) or listed in the U.S. Pharmacopeia or other generally recognized pharmacopeia for use in animals, and more particularly in humans.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin. Nutraceutical compositions can, but need not, comprise one or more active or inactive ingredients that are not necessarily considered pharmaceutically acceptable to current practitioners in the art.

Typical pharmaceutical or nutraceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical or nutraceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

The invention further encompasses administration of pharmaceutical or nutraceutical compositions and single unit dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The formulation should suit the mode of administration. In a preferred embodiment, the pharmaceutical or nutraceutical compositions and single unit dosage forms are sterile and prepared in a form suitable for administration to a subject, preferably an animal subject, more preferably a mammalian subject, and most preferably a human subject. Besides humans, preferred animal subjects include horses, birds, cats, dogs, rats, hamsters, mice, guinea pigs, cows, rabbits, and pigs.

A pharmaceutical or nutraceutical composition of the invention is formulated to be compatible with its intended route of administration. Examples of routes of administration include, but are not limited to, parenteral (for example, intravenous, intradermal, subcutaneous, intramuscular, subcutaneous, etc.), oral, buccal, sublingual, inhalation, intranasal, transdermal, topical, transmucosal, intra-tumoral, intra-synovial and rectal administration. In a specific embodiment, the composition is formulated in accordance with routine procedures as a pharmaceutical or nutraceutical composition adapted for intravenous, subcutaneous, intramuscular, oral, intranasal or topical administration to human beings. In an embodiment, a pharmaceutical or nutraceutical composition is formulated in accordance with routine procedures for oral administration to human beings. Typically, compositions for oral administration are solid dosage forms or solutions in sterile isotonic aqueous buffer.

Examples of dosage forms include, but are not limited to: tablets; caplets; capsules, such as soft elastic gelatin capsules or hard capsules; dropping pills; cachets; troches; lozenges; dispersions; suppositories; ointments; linimentums; cataplasms (poultices); pastes; powders; dressings; creams; plasters; solutions; patches; wound dressings; aerosols (for example, nasal sprays or inhalers); gels; liquid dosage forms suitable for oral or mucosal administration to a patient, including suspensions (for example, aqueous or non-aqueous liquid suspensions, oil-in-water emulsions, or a water-in-oil liquid emulsions), solutions, and elixirs; liquid dosage forms suitable for parenteral (for example, intravenous) administration to a patient; and sterile solids (for example, crystalline or amorphous solids or granular forms) that can be reconstituted to provide liquid dosage forms suitable for parenteral administration to a patient.

The composition, shape, and type of dosage forms of a solid dispersion composition of Dencichine will typically vary depending on their use. For example, a dosage form used in the acute treatment of a significant bleeding condition may contain larger amounts of a solid dispersion composition of Dencichine (for example, a damaged arteriole or vein) than a dosage form used in the chronic treatment of a minor bleeding condition (for example, a bleeding ulcer). Also, the therapeutically effective dosage form may vary among different types of bleeding conditions. Similarly, a parenteral dosage form may contain smaller amounts of one or more of the active ingredients than an oral dosage form used to treat the same disease or disorder. These and other ways in which specific dosage forms encompassed by this invention will vary from one another will be readily apparent to those skilled in the art. See, for example, Remington's Pharmaceutical Sciences, 18th ed., Mack Publishing, Easton Pa. (1990).

Bleeding conditions are generally emergencies requiring immediate action; therefore, immediate release and fast-acting formulations of a solid dispersion composition of Dencichine are generally preferred. Chronic bleeding conditions, such as hemorrhoids or bleeding ulcers, may benefit from administering formulations having slow-release, sustained release, or controlled-release characteristics of a solid dispersion composition of Dencichine. These various formulations are well within the grasp and practice of those having ordinary skill in the art.

Generally, the ingredients of compositions comprising a solid dispersion composition of Dencichine are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Pharmaceutical or nutraceutical compositions used in the methods of the invention that are suitable for oral administration can be presented as discrete dosage forms, such as, but are not limited to, tablets (for example, chewable tablets), caplets, capsules, grains, and liquids (for example, flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

In certain embodiments, the oral dosage forms are solid and prepared under anhydrous conditions with anhydrous ingredients, as described in detail in the sections above. However, the scope of the invention extends beyond anhydrous, solid oral dosage forms. As such, further forms are described herein.

Typical oral dosage forms are prepared by combining the active ingredient(s) (that is, the solid dispersion composition of Dencichine) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (for example, powders, tablets, capsules, and caplets) include, but are not limited to, starches, sugars, micro-crystalline cellulose, diluents, granulating agents, lubricants, binders, and disintegrating agents.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (for example, ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (for example, Nos. 2208, 2906, 2910), microcrystalline cellulose, and mixtures thereof.

Examples of fillers suitable for use in the pharmaceutical or nutraceutical compositions and dosage forms disclosed herein include, but are not limited to, talc, calcium carbonate (for example, granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103.TM. and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical or nutraceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical or nutraceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (for example, peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

The amount of the composition in the methods of the invention which will be effective in the prevention, treatment, management, or amelioration of a bleeding condition or one or more symptoms thereof will vary with the nature and severity of the disease or condition, and the route by which the active ingredient is administered. The frequency and dosage will also vary according to factors specific for each patient depending on the specific therapy (for example, therapeutic or prophylactic agents) administered, the severity of the bleeding disorder, hemorrhagic disease, or related condition, the route of administration, as well as age, body, weight, response, and the past medical history of the patient.

A therapeutically effective dose of the solid dispersion composition of Dencichine can be determined empirically, by conventional procedures known to those of skill in the art. See, for example, The Pharmacological Basis of Therapeutics, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans.

Effective doses for humans may be extrapolated from dose-response curves derived from in vitro or animal model test systems. For example, methods for the extrapolation of effective dosages in mice, and other animals, to humans are known to the art.

Typical dosage forms for administration in methods of the invention comprise a composition of the invention in an amount within the range of from about 1 mg to about 200 mg of solid dispersion composition of Dencichine. Particular dosage forms of the invention have incremental variations within this dosage range, including 2.0, 2.5, 3.0, 5.0, 7.5, 10.0, 15.0, 20.0, 25.0, 40.0, 50.0, 60.0, 75.0, 100, 125, 150, and 175 mg of solid dispersion composition of Dencichine, as well as incremental dosage variations thereof. A preferred dosage of solid dispersion composition of Dencichine, which would be amenable for human use, comprises from about 5 mg to about 20 mg, including incremental variations within this dosage range.

Exemplary dosage forms of the invention having a liquid formulation include 1, 3, 5, 7.5, 10, 15, 20, 50, 75, and 100 ml of a liquid composition (for example, water) of solid dispersion composition of Dencichine having a concentration ranging from about 0.05 mg/ml to about 25 mg/ml. The preferred concentrations of such liquid formulations will depend upon the dissolution characteristics of the medium, which will determine the upper limit of pharmaceutically acceptable concentrations of solid dispersion composition of Dencichine in such compositions. Consequently, alternative, pharmaceutically acceptable, concentrations of liquid formulations comprising solid dispersion compositions of Dencichine that are lower, as well as higher, than that stated herein are also contemplated by the present invention.

In the case of liquid dosage forms, suitable concentrations of solid dispersion compositions of Dencichine are suspended or dissolved in pharmaceutically acceptable carrier media, such as water, saline, and the like. Furthermore, suitable concentrations of solid dispersion compositions of Dencichine are suspended or dissolved under physiologically and physiochemically appropriate conditions.

Exemplary doses of a composition of the invention include microgram or milligram amounts of solid dispersion compositions of Dencichine per kilogram of subject or sample weight. For the compositions of the invention, the dosage administered to a patient can be administered from about 0.01 mg/kg to about 10 mg/kg. More preferably, the dosage of solid dispersion composition of Dencichine is from about 0.05 mg/kg to about 1.0 mg/kg.

The composition can be administered as a single once-a-day dose or as divided doses throughout a day. In some embodiments, the daily dose is administered twice daily in equally divided doses. In other embodiments, the daily dose is administered three times per day. In particular embodiments, the daily dose is administered three times per day in equally divided doses. In particular embodiments, the daily dose is administered four times per day in equally divided doses. The actual dosage can be determined by a practitioner of skill in the art according to, for example, the subjects age, body weight, body mass index, or other factors.

In certain embodiments, administration of a composition of the invention may be repeated daily. In certain embodiments, the administrations may be separated by at least 1 day, 2 days or 3 days.

Generally, however, the frequency of administering the solid dispersion composition of Dencichine depends on the need to treat a hemorrhagic condition or bleeding disorder. Consequently, administration of the solid dispersion composition of Dencichine typically ceases when the bleeding is arrested or brought under control by another means.

An effective amount of a composition described herein will provide therapeutic benefit without causing substantial toxicity. Toxicity of a composition can be determined by standard pharmaceutical procedures in cell cultures or experimental animals, for example, by determining the $LD_{50}$ (that is, the dose lethal to 50% of the population) or the $LD_{100}$ (that is, the dose lethal to 100% of the population).

The therapeutic index is the dose ratio between therapeutic effect and toxicity effect. Compounds which exhibit high therapeutic indices are preferred. The data obtained from these cell culture assays and animal studies can be used in formulating a dosage range that is not toxic for use in humans. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition and the type of bleeding indication to be treated. (See, for example, Fingl et al., 1996, In: The Pharmacological Basis of Therapeutics, 9.sup.th ed., Chapter 2, p. 29, Elliot M. Ross).

EXAMPLES

Example 1

Preparation of a Solid Dispersion Composition of Dencichine

The amounts of components provided for one preferred embodiment of a solid dispersion composition of Dencichine are illustrated in Table 1. The ratios of the illustrated amounts provide the preferred ratios of each of the components in the final preferred composition, as provided by one example that describes the method whereby the components are blended together to provide the solid dispersion composition of Dencichine.

TABLE 1

A Preferred Solid Dispersion Composition of Dencichine

| Component | Ingredient | Amount |
|---|---|---|
| Co-solvent | $(NH_4)_2CO_3$ | 0.8-80 g |
| | $H_2O$ | 80-8,000 ml |
| Active Ingredient | Dencichine | 2.0-20 g |
| Dispersion Supporter | PEG 6000 | 1.0-10 g |
| Cryoprotectant | Sucrose | 0.10-1.0 g |
| | Fucose | 0.10-1.0 g |

A preferred co-solvent is 1% aqueous ammonium carbonate (wt/vol), which was prepared by dissolving 0.8 g ammonium carbonate in 80 ml water. The active ingredient, Dencichine (2.0 g), was added to the prepared co-solvent/water solution, and the mixture was stirred to completely dissolve the Dencichine material, thereby providing a first solution. A preferred dispersive supporter, Polyethylene glycol 6000 (1.0 g), was added to the first solution and the mixture was stirred to effect dissolution, thereby providing a second solution. Finally, a preferred mixture of two cryoprotectants, sucrose (0.1 g) and fucose (0.1 g), was added to the resultant solution and the mixture was stirred to effect dissolution, thereby providing a third solution. The resultant solution was filtered and the filtrate was subjected to freeze-drying to provide the solid dispersion composition of Dencichine.

Example 2

Effect of the Solid Dispersion Composition of Dencichine on Rabbit Liver Hemorrhage Healthy rabbits having a weight of 2-2.5 kg were distributed randomly into four groups consisting of 6 rabbits per group. The rabbits in each group were fed only water for the twelve-hour period prior to operation. Each rabbit was anaesthetized by receiving an injection of sodium pentobarbital (30 mg/kg) in the abdominal cavity. An incision was made in the upper abdominal cavity of each animal and a piece of the liver was removed leaving a wound 2 cm in length, 1 cm in width and 0.5 cm in height. This type of wound resulted in one or more severed arterioles showing a spout-like bleeding.

At the time of wounding, the animals received by injection (2 ml/kg) via an ear vein one of following four compositions suspended in physiological saline: control, 0.5 KU/kg Reptilase, 25 mg/kg Sodium Dencichine, or 1 mg/kg solid dispersion composition of Dencichine prepared according to Example 1. Following the injection, the bleeding time and extent was recorded for each rabbit until the liver wound stopped bleeding.

The results demonstrated that the rabbits injected with the solid dispersion composition of Dencichine, the Sodium Dencichine, and the Reptilase significantly shortened the time and extent the wound bleeding, as compared to the physiological saline control group. The 1 mg/kg solid dispersion composition of Dencichine demonstrated comparable bleed cessation activity as observed with the 25 mg/kg dose of Sodium Dencichine.

Example 3

Effect of the Solid Dispersion Composition of Dencichine on Gastrorrhagia of Rats Healthy Sprague-Dawley rats having a weight of 180-220 g were distributed randomly into four groups consisting of 10 rats per group. The rats in each group were fed only water for the twelve-hour period prior to operation. Each rat was anaesthetized by receiving an injection of sodium pentobarbital (30 mg/kg) in the abdominal cavity. An incision was made in the upper abdominal cavity of each animal and the stomach exposed to air and minced along the greater curvature. The stomach was vacated for each animal and cleaned with sterile cotton swab.

The animals received by injection (1 ml/100 g) via a femoral vein one of following four compositions suspended in physiological saline: control, 0.5 KU/kg Reptilase, 25 mg/kg Sodium Dencichine, or 1 mg/kg solid dispersion composition of Dencichine prepared according to Example 1. Thirty minutes following the injection, one piece of the gastric body from each animal was excised using biopsy forceps to establish acute gastric bleeding. The bleeding time and extent was recorded for each rat until the wound stopped bleeding.

The results demonstrated that the rats injected with the solid dispersion composition of Dencichine, the Sodium Dencichine, and the Reptilase significantly shortened the time and extent the wound bleeding, as compared to the physiological saline control group. The 1 mg/kg solid dispersion composition of Dencichine demonstrated comparable bleed cessation activity as observed with the 25 mg/kg dose of Sodium Dencichine.

Example 4

Effect of the Solid Dispersion Composition of Dencichine on Tail Bleeding Time of Mouse Healthy male ICR mice having a weight of 18-22 g were distributed randomly into five groups consisting of 10 mice per group. The animals received by injection (0.1 ml/10 g) via the tail vein one of following four compositions suspended in physiological saline: control, 0.5 KU/kg Reptilase, 25 mg/kg Sodium Dencichine, or 1 mg/kg solid dispersion composition of Dencichine prepared according to Example 1. Thirty minutes following injection the tail of each mouse was cut 0.5 cm from the tail tip. The cut tail wound bleeding of each mouse was monitored by scrubbing the tail tip with a filter paper at timed intervals (30 s, 60 s, and every 10 s thereafter) until blood could not be seen on the filter paper.

The results demonstrated that the rats injected with the solid dispersion composition of Dencichine, the Sodium Dencichine, and the Reptilase significantly shortened the time required to stop the tail wound bleeding, as compared to the physiological saline control group. The 1 mg/kg solid dispersion composition of Dencichine demonstrated comparable bleed cessation activity as observed with the 25 mg/kg dose of Sodium Dencichine.

Example 5

Effect of the Solid Dispersion Composition of Dencichine on Whole Blood Coagulation Time of Rabbits (Tube Method)

Healthy rabbits were distributed randomly into three groups consisting of 5 rabbits per group. The animals received by injection (2 ml/kg) via an ear vein one of following three compositions suspended in physiological saline: control, 25 mg/kg Sodium Dencichine, or 1 mg/kg solid dispersion composition of Dencichine prepared according to Example 1.

Blood samples were drawn from the ear vein and placed into tubes 30 minutes before administration of the compositions and 60 minutes after administration of the compositions. The whole blood coagulation time was recorded by inclining the tube at a 30 degree angle every 30 seconds to determine its flowable characteristics. This action was repeated until the blood stopped flowing and became totally coagulated, as adjudged by the inability of blood to flow along the sides of the tube when the tube was inverted at a 90 degree angle. The time required to attain total coagulation of the blood was record once all blood flow along the sides of the tube stopped.

The results showed that after the intravenous injection of the three compositions into rabbits, both 25 mg/kg Dencichine sodium salt and 1 mg/kg solid dispersion composition of Dencichine demonstrated significantly shorter coagulation times by this assay that lasted at least 60 minutes, as compared to the results obtained with the physiological saline control. The 1 mg/kg solid dispersion composition of Dencichine demonstrated comparable blood coagulation activity as observed with the 25 mg/kg dose of Sodium Dencichine.

Example 6

Effect of the Solid Dispersion Composition of Dencichine on Effect on Fibrinolytic Activity Healthy rabbits having weight of 2.0-2.5 kg were distributed randomly into three groups consisting of 4 rabbits per group. Each animal received by injection (10 ml) via an ear vein one of following three compositions suspended in physiological saline: control, 25 mg/kg Sodium Dencichine, or 1 mg/kg solid dispersion composition of Dencichine prepared according to Example 1. Blood was collected via carotid artery from each rabbit 30 min and 60 min after administration of the compositions. The blood samples were placed into the silicified centrifuge tube containing 3.8% sodium citrate anti-coagulant (1:9 anticoagulant:blood volume ratio). The tubes were centrifuged for 10 min at 3,000 rpm at 4° C. The platelet poor plasma was collected and stored on ice.

An aliquot of the platelet poor plasma (0.5 ml) and cold distilled water (9 ml) were mixed in a conical centrifuge tube at 4° C. A 1% (vol/vol) acetic acid solution (0.10 ml) was mixed into this solution, and the mixture was incubated for 15 min at 4° C. The euglobulin precipitate was separated from the solution by centrifugation for 5 min at 3,000 rpm. The supernatant was discarded, and the euglobulin precipitate was dried 2 min.

A solution (0.5 ml) of aqueous boric acid/sodium borate (pH=9.0) was added to the euglobulin precipitate to effect dissolution. A 25 mM $CaCl_2$ solution was added to the dissolved euglobulin solution to form the fibrin clot. The time required to dissolve the fibrin clot (euglobulin lysis time) was recorded. The results showed that both 25 mg/kg Dencichine sodium salt and 1 mg/kg solid dispersion composition of Dencichine significantly extended the euglobulin lysis time, as compared to the physiological saline control. The 1 mg/kg solid dispersion composition of Dencichine demonstrated comparable effects on extending the euglobulin lysis time as observed with the 25 mg/kg dose of Sodium Dencichine.

Example 7

Preparation of Preferred Solid Dispersion Compositions of Dencichine Containing a Cryoprotectant Recipe A:

| Component | Ingredient | Amount |
|---|---|---|
| Co-solvent | $(NH_4)_2CO_3$ | 0.80 g |
|  | $H_2O$ | 80 ml |
| Active Ingredient | Dencichine | 2.0 g |
| Dispersion Supporter | PEG 6000 | 1.0 g |
| Cryoprotectant | Sucrose | 0.10 g |
|  | Fucose | 0.10 g |

Recipe B:

| Component | Ingredient | Amount |
|---|---|---|
| Co-solvent | $(NH_4)_2CO_3$ | 0.80 g |
|  | $H_2O$ | 80 ml |
| Active Ingredient | Dencichine | 2.0 g |
| Dispersion Supporter | Polylactic acid | 2.0 g |
| Cryoprotectant | Sucrose | 0.20 g |

Recipe C:

| Component | Ingredient | Amount |
|---|---|---|
| Co-solvent | $(NH_4)_2CO_3$ | 0.80 g |
|  | $H_2O$ | 80 ml |
| Active Ingredient | Dencichine | 2.0 g |
| Dispersion Supporter | Gelatin | 4.0 g |
|  | NaOH (20% (wt/vol)) | 4.5 ml |
| Cryoprotectant | Fucose | 0.20 g |

Recipe D:

| Component | Ingredient | Amount |
|---|---|---|
| Co-solvent | $(NH_4)_2CO_3$ | 0.80 g |
|  | $H_2O$ | 80 ml |
| Active Ingredient | Dencichine | 2.0 g |

-continued

| Component | Ingredient | Amount |
|---|---|---|
| Dispersion Supporter | Stearic acid | 2.0 g |
| | 1.5% (wt/vol) poloxamer P 188 | 4.5 ml |
| Cryoprotectant | Sucrose | 0.20 g |

Recipe E:

| Component | Ingredient | Amount |
|---|---|---|
| Co-solvent | $(NH_4)_2CO_3$ | 0.80 g |
| | $H_2O$ | 80 ml |
| Active Ingredient | Dencichine | 2.0 g |
| Dispersion Supporter | Stearic acid | 2.0 g |
| | Glycerol Monostearate | 2.4 g |
| | PEG 6000 | 2.0 g |
| Cryoprotectant | Fucrose | 0.20 g |

Recipe F:

| Component | Ingredient | Amount |
|---|---|---|
| Co-solvent | $(NH_4)_2CO_3$ | 0.80 g |
| | $H_2O$ | 80 ml |
| Active Ingredient | Dencichine | 2.0 g |
| Dispersion Supporter | Sodium Alginate | 2.0 g |
| | Water-soluble chitosan | 2.0 g |
| Cryoprotectant | Sucrose | 0.20 g |

Recipe G:

| Component | Ingredient | Amount |
|---|---|---|
| Co-solvent | $(NH_4)_2CO_3$ | 0.80 g |
| | $H_2O$ | 80 ml |
| Active Ingredient | Dencichine | 2.0 g |
| Dispersion Supporter | Water-soluble chitosan | 2.0 g |
| | Sodium triphosphate | 0.25 g |
| Cryoprotectant | Sucrose | 0.10 g |
| | Fucose | 0.10 g |

In recipes A-G, the solid dispersion composition of Dencichine is prepared in the following manner. The co-solvent was prepared initially by dissolving the ammonium carbonate into water. The active ingredient (Dencichine) was added to the co-solvent/water solution and the mixture was stirred to effect dissolution, thereby providing a first solution. The dispersion supporter was added to the first solution and the mixture was stirred to effect dissolution, thereby providing a second solution. The cryoprotectant was added to the second solution and the mixture was stirred to effect dissolution, thereby providing a third solution. The third solution is filtered to remove any particulate matter, and the resultant filtrate was subjected to freeze-drying to provide the solid dispersion composition of Dencichine.

Example 8

Preparation of Preferred Solid Dispersion Compositions of Dencichine Lacking Cryoprotectant A preferred solid dispersion composition of Dencichine lacking a cryoprotectant is prepared according to the following method.

TABLE 2

A Preferred Solid Dispersion Composition of Dencichine

| Component | Ingredient | Amount |
|---|---|---|
| Co-solvent | $NH_4OH$ | 0.15-15 g |
| | $H_2O$ | 15-1,500 ml |
| Active Ingredient | Dencichine | 1.0-100 g |
| Dispersion Supporter | Mannitol | 1.0-100 g |
| | $H_2O$ | 30-3,000 ml |

A preferred co-solvent is 1% aqueous ammonium hydroxide (wt/vol), which was prepared by dissolving ammonium hydroxide (0.15 g) in water (15 ml). The active ingredient, Dencichine (1.0 g), was added to the prepared co-solvent/water solution, and the mixture was stirred to completely dissolve the Dencichine, thereby providing a first solution. A preferred dispersive supporter, mannitol (1.0 g), was dissolved in water (30 ml). The mixture was stirred to effect dissolution, thereby yielding a second solution. The first solution is slowly added to the second solution, and the mixture is stirred 10 to 60 min. A sufficient quantity of water is then added to the resultant mixture with stirring until a final solution weight of 100 g is achieved, thereby yielding a third solution. The resultant third solution is filtered to remove any insoluble particulate matter, thereby providing a filtrate. The filtrate is subjected to −40° C. for twenty-four hours and then subjected to freeze-drying to provide the solid dispersion composition of Dencichine.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A method of treating a bleeding condition in a subject in need thereof, comprising administering a composition comprising a therapeutically effective amount of Dencichine, a co-solvent, and a dispersion supporter.

2. The method of claim 1, wherein the composition further comprises a cryoprotectant.

3. The method of claim 1, wherein a therapeutically effective amount of Dencichine comprises from about 1 mg to about 200 mg of Dencichine.

4. The method of claim 1, wherein administering a composition comprises ingesting an oral formulation, injecting a peritoneal formulation, or applying a topical formulation.

5. The method of claim 1, wherein the subject comprises at least one member selected from the group consisting of human, horse, bird, cat, dog, rat, hamster, mouse, guinea pigs, cow, rabbit, and pig.

6. The method of claim 1, wherein the subject is a human.

7. The method of claim 6, wherein the therapeutically effective amount of Dencichine comprises from about 2.5 mg to about 10 mg of Dencichine.

* * * * *